United States Patent
Lao et al.

(10) Patent No.: US 9,567,635 B2
(45) Date of Patent: Feb. 14, 2017

(54) HOT START REVERSE TRANSCRIPTION BY PRIMER DESIGN

(71) Applicant: APPLIED BIOSYSTEMS, LLC, Carlsbad, CA (US)

(72) Inventors: Kai Lao, Pleasanton, CA (US); Neil Straus, Emeryville, CA (US); Kenneth Livak, Arlington, MA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/656,626

(22) Filed: Mar. 12, 2015

(65) Prior Publication Data

US 2015/0252418 A1    Sep. 10, 2015

Related U.S. Application Data

(63) Continuation of application No. 12/504,633, filed on Jul. 16, 2009, now Pat. No. 8,993,240, which is a continuation of application No. 11/458,081, filed on Jul. 17, 2006, now abandoned.

(60) Provisional application No. 60/699,967, filed on Jul. 15, 2005.

(51) Int. Cl.
| | |
|---|---|
| *C07H 21/02* | (2006.01) |
| *C07H 21/04* | (2006.01) |
| *C12N 9/00* | (2006.01) |
| *C12Q 1/68* | (2006.01) |

(52) U.S. Cl.
CPC ............ *C12Q 1/6876* (2013.01); *C07H 21/04* (2013.01); *C12Q 1/6844* (2013.01); *C12Q 1/6848* (2013.01); *C07H 21/02* (2013.01); *C12N 9/00* (2013.01); *C12Q 1/686* (2013.01)

(58) Field of Classification Search
None
See application file for complete search history.

(56) References Cited

U.S. PATENT DOCUMENTS

| | | |
|---|---|---|
| 5,837,442 A | 11/1998 | Tsang et al. |
| 6,365,729 B1 | 4/2002 | Tyagi et al. |
| 2001/0012617 A1 | 8/2001 | Hayashizaki |
| 2004/0067492 A1 | 4/2004 | Peng et al. |
| 2004/0142369 A1 | 7/2004 | Alajem et al. |
| 2004/0171039 A1 | 9/2004 | Bruchez et al. |
| 2005/0042666 A1 | 2/2005 | Nazarenko et al. |
| 2005/0153916 A1 | 7/2005 | McSwiggen et al. |
| 2006/0057595 A1* | 3/2006 | Lao .............. C12Q 1/6851 435/6.12 |
| 2015/0252418 A1* | 9/2015 | Lao .............. C12Q 1/6844 435/6.11 |

FOREIGN PATENT DOCUMENTS

EP    1152062 A2    11/2001

OTHER PUBLICATIONS

Ailenberg et al. Controlled hot start and improved specificity in carrying out PCR utilizing touch-up and loop incorporated primers (TULIPS). BioTechniques (2000) vol. 29, No. 5, pp. 1018-1024.*
Kaboev et al. PCR hot start using primers with the structure of molecular beacons (hairpin-like structure). Nucleic Acids Res. (2000) vol. 28, No. 21, e94, pp. 1-2.*
PCT/US2006/027753; International Search Report & Written Opinion mailed Aug. 6, 2007, 3 pages.

* cited by examiner

*Primary Examiner* — David Thomas

(57) ABSTRACT

The present teachings provide methods, compositions, and kits for performing primer extension reactions. In some embodiments, a reverse transcription reaction is performed on a target polynucleotide with a hot start primer comprising a blunt-ended self-complementary stem, and a loop, and extension products form at high temperatures but reduce extension product formation at low temperatures.

19 Claims, 1 Drawing Sheet

SEQUENCE LISTING

<160> NUMBER OF SEQ ID NOS: 7

<210> SEQ ID NO 1
<211> LENGTH: 15

```
<212> TYPE: DNA
<213> ORGANISM: Homo sapiens

<400> SEQUENCE: 1
ccccgcgagc acaga                                                   15

<210> SEQ ID NO 2
<211> LENGTH: 19
<212> TYPE: DNA
<213> ORGANISM: Homo sapiens

<400> SEQUENCE: 2
ccacgatgga ggggaagac                                               19

<210> SEQ ID NO 3
<211> LENGTH: 33
<212> TYPE: DNA
<213> ORGANISM: Homo sapiens

<400> SEQUENCE: 3
gtcttcccct ccttccacga tggaggggaa gac                               33

<210> SEQ ID NO 4
<211> LENGTH: 31
<212> TYPE: DNA
<213> ORGANISM: Homo sapiens

<400> SEQUENCE: 4
gtcttcccct ttccacgatg gaggggaaga c                                 31

<210> SEQ ID NO 5
<211> LENGTH: 29
<212> TYPE: DNA
<213> ORGANISM: Homo sapiens

<400> SEQUENCE: 5
gtcttccctt ccacgatgga ggggaagac                                    29

<210> SEQ ID NO 6
<211> LENGTH: 27
<212> TYPE: DNA
<213> ORGANISM: Homo sapiens

<400> SEQUENCE: 6
gtcttcttcc acgatggagg ggaagac                                      27

<210> SEQ ID NO 7
<211> LENGTH: 14
<212> TYPE: DNA
<213> ORGANISM: Homo sapiens

<400> SEQUENCE: 7
ctttgccgat ccgc                                                    14
```

HOT START REVERSE TRANSCRIPTION BY PRIMER DESIGN

CROSS-REFERENCE TO RELATED APPLICATIONS

Figure 1A:
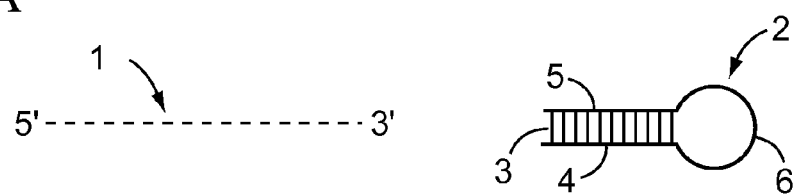

This application is a continuation of U.S. application Ser. No. 12/504,633, filed on Jul. 16, 2009, which is a continuation of U.S. application Ser. No. 11/458,081, filed on Jul. 17, 2006 (now abandoned), which claims a benefit of priority under 35 U.S.C. §119(e) from U.S. Application No. 60/699,967, filed on Jul. 15, 2005, the contents of all of which are incorporated herein by reference.

FIELD

The present teachings relate to methods of synthesizing nucleic acids by primer extension.

INTRODUCTION

The integrity of primer-mediated methods of synthesizing nucleic acids can be compromised by non-specific hybridization of primer to inappropriate target polynucleotides. The analysis of nucleic acids is benefited by approaches by approaches that minimize the generation of mis-extension products. For example, 'hot start' approaches have been employed in PCR, where inhibition of polymerase activity has been achieved. For example, U.S. Pat. No. 5,338,671 describes the use of antibodies specific for a thermostable DNA polymerase to inhibit the DNA polymerase activity at low temperatures. Chemical treatment with citraconic anhydride is another way hot start PCR has been achieved (see U.S. Pat. No. 5,773,258 and U.S. Pat. No. 5,677,152). Hot start methods which use a heat labile material, such as wax, to separate or sequester reaction components are described in U.S. Pat. No. 5,411,876. The application of such hot start approaches to reverse transcription have proven challenging. For example, many reverse transcriptases are not heat-stabile.

SUMMARY

The present teachings provide a method for reducing the formation of primer extension products at a low temperature but allowing the formation of primer extension products at a high temperature comprising; forming a reaction mixture at the low temperature below about 27 C, wherein the reaction mixture comprises a target polynucleotide, a primer extending enzyme, and a hot start primer, wherein the hot start primer comprises a loop and a self-complementary stem, wherein a target-specific region of the self-complementary stem comprises a sequence of at least six nucleotides that are complementary with the target polynucleotide, wherein the target-specific region of the self-complementary stem is substantially hybridized with a quencher region in the self-complementary stem when at the low temperature and wherein the self-complementary stem is substantially unable to hybridize with the target polynucleotide when at the low temperature; elevating the temperature of the reaction mixture to a high temperature between 35 C-60 C, wherein the target-specific region of the self-complementary stem is substantially unhybridized with the quencher region in the self-complementary stem at the high temperature, and wherein the target-specific region hybridizes to the target polynucleotide; extending the target-specific region of the self-complementary stem with the primer extending enzyme to form a primer extension product; and, generating a primer extension product at the high temperature but not at the low temperature.

In some embodiments, the present teachings provide a composition comprising a target polynucleotide and a hot start primer, wherein the hot start primer comprises a self-complementary stem, wherein the self-complementary stem comprises a target-specific region and a quencher region, wherein the target-specific region comprises at least six nucleotide s, wherein the target-specific region is substantially unhybridized with the quencher region in the self-complementary stem, and wherein the target-specific region is hybridized with the target polynucleotide.

In some embodiments, the present teachings provide a kit for reducing the formation of primer extension products at a low temperature but allowing the formation of primer extension products at a high temperature comprising; a hot start primer, a primer extending enzyme, a primer extending enzyme buffer, and dNTPs, wherein the hot start primer comprises a loop and a self-complementary stem, wherein the self-complementary stem comprises a target-specific region that is at least six nucleotide s in length, wherein the target-specific region is complementary to target polynucleotide, and wherein the target-specific region is substantially hybridized to a quencher region when at a temperature of 27 C or lower.

These and other features of the present teachings are set forth herein.

DRAWINGS

Figure 1B:
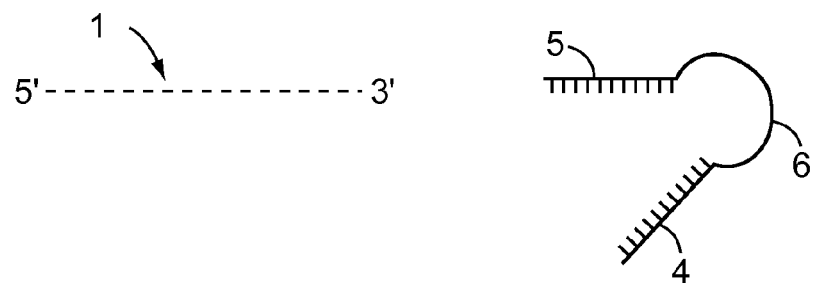
Figure 1C:
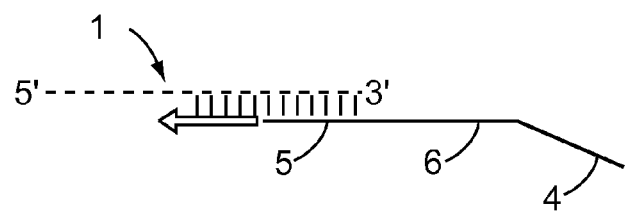

FIGS. 1A, 1B and 1C depict one illustrative embodiment according to the present teachings.

DESCRIPTION OF EXEMPLARY EMBODIMENTS

It is to be understood that both the foregoing general description and the following detailed description are exemplary and explanatory only and are not intended to limit the scope of the current teachings. In this application, the use of the singular includes the plural unless specifically stated otherwise. For example, "a forward primer" means that more than one forward primer can be present; for example, one or more copies of a particular forward primer species, as well as one or more different forward primer species. Also, the use of "comprise", "contain", and "include", or modifications of those root words, for example but not limited to, "comprises", "contained", and "including", are not intended to be limiting. The term and/or means that the terms before and after can be taken together or separately. For illustration purposes, but not as a limitation, "X and/or Y" can mean "X" or "Y" or "X and Y".

The section headings used herein are for organizational purposes only and are not to be construed as limiting the described subject matter in any way. All literature and similar materials cited in this application, including, patents, patent applications, articles, books, treatises, and internet web pages are expressly incorporated by reference in their entirety for any purpose. In the event that one or more of the incorporated literature and similar defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

SOME DEFINITIONS

As used herein, the term "denaturing" refers to the melting of two complementary nucleic acid strands, and is typically achieved by elevating the temperature. In some embodiments, denaturing can be achieved by the addition of base (e.g. —NaOH) or other approaches for dissociating nucleic acids that are familiar to one of ordinary skill in the art of molecular biology.

As used herein, the term "complementary" refers to nucleic acid sequences that are capable of forming Watson-Crick base-pairs. For example, a self-complementary primer comprises a self-complementary stem which is capable of forming Watson-Crick base-pairs with itself at a low temperature. When at the low temperature, the strands of such a self-complementary stem are said to be hybridized to one another. When at a high temperature, the strands of such a self-complementary stem are not hybridized to each other, and the target specific region of the self-complementary stem can be hybridized with a target. In this application, a statement that one sequence is complementary to another sequence encompasses situations in which the two sequences have slight mismatches. Here, the term "sequence" encompasses, but is not limited to, nucleic acid sequences, polynucleotides, oligonucleotides, probes, primers, primer-specific regions, and target-specific regions. Despite the mismatches, the two sequences should selectively hybridize to one another under appropriate conditions.

As used herein, the term "hot start primer" refers to a primer comprising a self-complementary stem and a loop, wherein the self-complementary stem comprises a target specific region and a quencher region. At low temperatures, the target-specific region is hybridized to the quencher region. At high temperatures, the target-specific region is not hybridized to the quencher region, and can hybridize to the corresponding target polynucleotide, thereby allowing for a hot start extension reaction. In some embodiments, the self-complementary stem is blunt-ended, such that there is not a nucleotide overlap at the 5' or 3' end of the self-complementary stem. In some embodiments, the mRNA primer comprises a nearly blunt-ended self-complementary stem, such as for example a single 3' nucleotide overhang. Generally, such 3' overhangs will be of minimal length to avoid undesired priming on targets prior to the melting of the self-complementary stem region by the high temperature. Overhangs on the 5' end are generally more tolerable, since extension does not proceed from the 5' of a sequence.

As used herein, the term "target polynucleotide" refers to a polynucleotide sequence that is sought to be reverse transcribed. The target polynucleotide can be obtained from any source, and can comprise any number of different compositional components. For example, the target can be nucleic acid (e.g. DNA or RNA), transfer RNA, sRNA, and can comprise nucleic acid analogs or other nucleic acid mimic, though typically the target will be messenger RNA (mRNA) and/or micro RNA (miRNA). The target can be methylated, non-methylated, or both. The target can be bisulfite-treated and non-methylated cytosines converted to uracil. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in for example but not limited to forensics samples (see for example Butler, 2001, *Forensic DNA Typing: Biology and Technology Behind STR Markers*. The target polynucleotides of the present teachings can be derived from any of a number of sources, including without limitation, viruses, prokaryotes, eukaryotes, for example but not limited to plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells, and lysed cells. It will be appreciated that target polynucleotides can be isolated from samples using any of a variety of procedures known in the art, for example the Applied Biosystems ABI Prism™ 6100 Nucleic Acid PrepStation, and the ABI Prism™ 6700 Automated Nucleic Acid Workstation, Boom et al., U.S. Pat. No. 5,234,809, mirVana RNA isolation kit (Ambion), etc. It will be appreciated that target polynucleotides can be cut or sheared prior to analysis, including the use of such procedures as mechanical force, sonication, restriction endonuclease cleavage, or any method known in the art. In general, the target polynucleotides of the present teachings will be single stranded, though in some embodiments the target polynucleotide can be double stranded, and a single strand can result from denaturation.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226). Exemplary LNA sugar analogs within a polynucleotide include, but are not limited to, the structures:

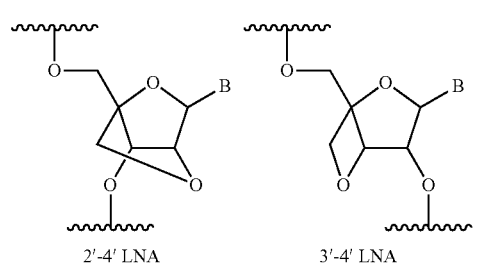

2'-4' LNA      3'-4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N^9$-position of the nucleotide base. When the nucleotide base is pyrimidine, e.g. C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) *DNA Replication, $2^{nd}$ Ed.*, Freeman, San Francisco, Calif.).

One or more of the pentose carbons of a nucleotide may be substituted with a phosphate ester having the formula:

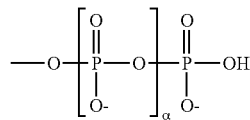

where α is an integer from 0 to 4. In certain embodiments, a is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see: Shabarova, Z. and Bogdanov, A. *Advanced Organic Chemistry of Nucleic Acids*, VCH, New York, 1994.

Some Specific Exemplary Embodiments

FIGS. 1A, 1B and 1C depict an illustrative relationship between a hot start primer and a target polynucleotide according to some embodiments of the present teachings. In (A), a target polynucleotide (1) is shown with a hot start primer (2) in a reaction mixture at a low temperature (for example 25 C, roughly room temperature). The hot start primer (2) comprises a self-complementary stem (3) comprising a target-specific region (4) and a quencher region (5). The hot start primer also comprises a loop (6). In (B), elevation to a high temperature is performed (for example 42 C, an appropriate temperature for a reverse transcriptase), and the stem of the hot start primer melts, thereby liberating the target-specific region (5) of the self-complementary primer. In (C), the target-specific region (5) of the hot start primer can hybridize to the target polynucleotide (1), and extension of the primer by the reverse transcriptase can occur (bold arrow).

In some embodiments, the architecture of the hot start primer can differ from that depicted in FIGS. 1A, 1B and 1C. For example, the loop (6) of the hot start primer shown in FIGS. 1A, 1B and 1C can itself form part of the target-specific region of the hot start primer. It will be appreciated that one of skill in the art would be able to make these and other minor modifications in the design of the hot start primer provided by the present teachings, and still be within their scope.

In some embodiments, the reverse transcription is set up at room temperature. In some embodiments, the reverse transcription is set up at 20 C-27 C. In some embodiments, the reverse transcription can be set up on ice. In some embodiments, the reverse transcription reaction can be set up at 4 C-27 C.

Certain methods of optimizing reverse transcription and amplification reactions are known to those skilled in the art. For example, it is known that PCR may be optimized by altering times and temperatures for annealing, polymerization, and denaturing, as well as changing the buffers, salts, and other reagents in the reaction composition. Optimization may also be affected by the design of the amplification primers used. For example, the length of the primers, as well as the G-C:A-T ratio may alter the efficiency of primer annealing, thus altering the amplification reaction. Descriptions of amplification optimization can be found in, among other places, James G. Wetmur, "Nucleic Acid Hybrids, Formation and Structure," in Molecular Biology and Biotechnology, pp. 605-8, (Robert A. Meyers ed., 1995); McPherson, particularly in Chapter 4; Rapley; and Protocols & Applications Guide, rev. September 2004, Promega.

In some embodiments, the present teachings contemplate single-tube RT-PCR approaches, and discussed for example in Mohamed et al., (2004) Journal of Clinical Virology, 30:150-156. In some embodiments, the reverse transcription products of the present teachings can be amplified in a multiplexed pre-amplifying PCR followed by a plurality of lower-plex decoding PCRs, as described for example in WO2004/051218 to Andersen and Ruff, U.S. Pat. No. 6,605, 451 to Xtrana, and U.S. Non-Provisional application Ser. No. 11/090,830 to Andersen et al., and U.S. Non-Provisional application Ser. No. 11/090,468 to Lao et al., Generally, the length of the stem of the hot start primer can vary according to the context of the application. For example, when the target-specific region of the hot start primer is G:C rich, the length of the stem region can be shorter. Conversely, when the target-specific region of the hot start primer is A:T rich, the length of the stem region can be longer. Such procedures can be employed to adjust the length of the stem to correspond with a desired Tm, given a particular reaction context at hand. In some embodiments, the length of the stem is between 6-12 nucleotide base-pairs.

Generally, the length of the loop of the hot start primer will be between 8-24 nucleotides in length. Generally, short loops can have the beneficial effect of minimizing the likelihood of loop sequence displacing stem sequence at lower reaction temperatures. It will be appreciated by one of ordinary skill in the art that a variety of stem-loop configurations are available and within routine experimentation.

Illustrative molecular biology techniques of ready availability to one of skill in the art can be found in Sambrook et al., Molecular Cloning, 3rd Edition.

CERTAIN EXEMPLARY KITS

The instant teachings also provide kits designed to expedite performing certain of the disclosed methods. Kits may serve to expedite the performance of certain disclosed methods by assembling two or more components required for carrying out the methods. In certain embodiments, kits contain components in pre-measured unit amounts to minimize the need for measurements by end-users. In some embodiments, kits include instructions for performing one or more of the disclosed methods. Preferably, the kit components are optimized to operate in conjunction with one another.

Thus, in some embodiments the present teachings provide a kit for reducing primer extension products at a low temperature and allowing primer extension at a high temperature comprising; a hot start primer, a primer extending enzyme, a primer extending enzyme buffer, and dNTPs, wherein the hot start primer comprises a loop and a self-complementary stem, wherein the self-complementary stem comprises a target-specific region that is at least six nucleotides in length, wherein the target-specific region is complementary to target polynucleotide, wherein the target-specific region is substantially hybridized to a quencher region when at a temperature of 27 C or lower, and wherein the target-specific region when hybridized to the quencher region forms a blunt end structure, a structure with a one nucleotide overlap, or a structure with a two nucleotide overlap. In some embodiments, the primer extending enzyme is a reverse transcriptase. In some embodiments, the loop of the hot start primer comprises 8-24 nucleotides. In some embodiments, the self-complementary stem of the hot start primer comprises 6-12 nucleotide base-pairs. In some embodiments, the kit further comprises a forward primer and reagents for performing a PCR. In some embodiments, the reagents for performing the PCR are included in a vessel that is the same vessel that contains at least one of the hot start primer, the primer extending enzyme, the primer extending enzyme buffer, and the dNTPs. In some embodiments, the target polynucleotide is selected from the group comprising messenger RNA, small non-coding RNA, and micro RNA.

The current teachings, having been described above, may be better understood by reference to examples. The following examples are intended for illustration purposes only, and should not be construed as limiting the scope of the teachings herein in any way.

EXAMPLE

An illustrative experiment was performed comprising the primer and probe sequences found in Table 1 below directed to the ACTB messenger RNA. The results of different RT reactions using different RT primers, and reaction temperatures, were quantitated using real-time PCR with a forward primer FP-ACTB (SEQ ID NO:1), a reverse primer RP-ACTB (SEQ ID NO:2), and a TaqMan 5' nuclease probe Taq-ACTB (SEQ ID NO:7) There were two reverse transcription temperature conditions: a low temperature RT at 20 C, and a high temperature RT at 40 C. There were six RT reactions compared for each of the two temperature conditions, using the following six conditions.

1) RT linear primer (SEQ ID NO:2).
2) RT hot start primer with 8 base-pair stem (SEQ ID NO: 5.
3) RT hot start primer with 10 base-pair stem (SEQ ID NO:4).
4) RT hot start primer with 12 base-pair stem (SEQ ID NO:3).
5) buffer alone (no RT primer).
6) No template control.

| SEQ ID | Oligo Name | Sequence |
|---|---|---|
| SEQ ID NO: 1 | FP-ACTB | CCCCGCGAGCACAGA |
| SEQ ID NO: 2 | RP-ACTB | CCACGATGGAGGGGAAGAC |
| SEQ ID NO: 3 | RP-ACTB-12 | GTCTTCCCCTCCTTCCACGATGGAGGGGAAGAC |
| SEQ ID NO: 4 | RP-ACTB-10 | GTCTTCCCCTTTCCACGATGGAGGGGAAGAC |
| SEQ ID NO: 5 | RP-ACTB-8 | GTCTTCCCTTCCACGATGGAGGGGAAGAC |
| SEQ ID NO: 6 | RP-ACTB-6 | GTCTTCTTCCACGATGGAGGGGAAGAC |
| SEQ ID NO: 7 | Taq-ACTB | (6-FAM) CTTTGCCGATCCGC (MGB) |

The experiment was set up at room temperature. The RT reaction was done following manufacture's suggestion by using of Applied Biosystems High Capacity cDNA Archive Kit (CN: 4322171). In the low temperature condition, the reverse transcription reaction was performed at 20 C for 30 minutes. In the high temperature condition, the reverse transcription was performed at 40 C for 30 minutes.

Ct values derived from TaqMan™ quantitative PCR using ABI TaqMan universal PCR master mix demonstrated a hot start effect for hot start primers comprising a self-complementary stem. Specifically, the fold reduction of RT product of linear primer to hot start primer at 20 C was significantly greater than the fold reduction of RT product of linear primer to hot start primer at 40 C, thus illustrating inhibition of reverse transcription by the presence of the hot-start primer comprising the self-complementary stem. Further, hot start primers with longer self-complementary stems showed a stronger hot start effect than primers with shorter self-complementary stems. Thus, for example, the RT primer with a twelve nucleotide base-pair stem showed a stronger reduction in RT product formed at 20 C compared to a linear RT primer, than did an eight nucleotide base-pair stem RT primer in the 20 C RT reaction compared to the linear RT primer.

Although the disclosed teachings have been described with reference to various applications, methods, and kits, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

We claim:

1. A composition comprising an RNA target, a reverse transcriptase, and a hot start reverse transcriptase (RT) primer, wherein the hot start RT primer comprises a sequence that forms a loop and a self-complementary stem at a temperature of 27° C. or lower, wherein the self-complementary stem, when formed, comprises a target-specific region hybridized to a quencher region, wherein the target-specific region is substantially unhybridized with the quencher region in the self-complementary stem at a temperature between 35° C. to 60° C., and wherein the target-specific region is hybridized with the RNA target.

2. The composition according to claim 1 wherein the RNA target is a messenger RNA.

3. The composition according to claim 1 wherein the RNA target is a small non-coding RNA.

4. The composition according to claim 3 wherein the small non-coding RNA is a micro RNA.

5. The composition according to claim 1 wherein the loop comprises 8-24 nucleotides.

6. The composition according to claim 1 wherein the self-complementary stem comprises 6-12 nucleotide base-pairs.

7. The composition according to claim 1 wherein the target-specific region further comprises at least one nucleotide present in the loop.

8. The composition according to claim 1 wherein the target-specific region, when hybridized to the quencher region, forms a blunt-ended structure.

9. A kit for reducing primer extension products at a low temperature and allowing primer extension at a high temperature comprising;
a hot start reverse transcriptase (RT) primer, a reverse transcriptase, a buffer, and dNTPs, wherein the hot start RT primer comprises a sequence that forms a loop and a self-complementary stem at a temperature of 27° C. or lower, wherein the self-complementary stem, when formed, comprises a target-specific region hybridized to a quencher region, wherein the target-specific region is complementary to an RNA target, and wherein the target-specific region when hybridized to the quencher region forms a blunt-ended structure, a structure with a one-nucleotide overhang, or a structure with a two-nucleotide overhang.

10. The kit according to claim 9 wherein the loop comprises 8-24 nucleotides.

11. The kit according to claim 9 wherein the self-complementary stem comprises 6-12 nucleotide base-pairs.

12. The kit according to claim 9 further comprising a second primer that selectively hybridizes to a DNA target and reagents for performing a polymerase chain reaction (PCR).

13. The kit according to claim 12 wherein the reagents for performing the PCR are included in a vessel that is the same vessel that contains at least one of the hot start RT primer, the reverse transcriptase, the buffer, and the dNTPs.

14. The kit according to claim 9 wherein the RNA target is selected from the group comprising a messenger RNA, a small non-coding RNA, and a micro RNA.

15. The composition according to claim 1 wherein the target-specific region comprises at least six nucleotides.

16. The kit according to claim 9 wherein the target-specific region comprises at least six nucleotides.

17. The kit according to claim 12 wherein the primer that selectively hybridizes to a DNA target is a hot start primer.

18. The kit of claim 9, wherein the one-nucleotide overhang or the two-nucleotide overhang is at the 5' end of the hot start RT primer.

19. The kit of claim 9, wherein the one-nucleotide overhang or the two-nucleotide overhang is at the 3' end of the hot start RT primer.

* * * * *